US012447250B2

(12) United States Patent
Zafiris

(10) Patent No.: US 12,447,250 B2
(45) Date of Patent: Oct. 21, 2025

(54) PERITONEAL DIALYSIS SYSTEM USING PRESSURIZED CHAMBER AND PUMPING BLADDER

(71) Applicants: BAXTER INTERNATIONAL INC., Deerfield, IL (US); BAXTER HEALTHCARE SA, Glattpark (CH)

(72) Inventor: John Zafiris, Hawthorn Woods, IL (US)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 1106 days.

(21) Appl. No.: 17/400,688

(22) Filed: Aug. 12, 2021

(65) Prior Publication Data

US 2022/0054723 A1 Feb. 24, 2022

Related U.S. Application Data

(60) Provisional application No. 63/067,006, filed on Aug. 18, 2020.

(51) Int. Cl.
*A61M 1/28* (2006.01)
*A61M 1/16* (2006.01)

(52) U.S. Cl.
CPC ............ *A61M 1/28* (2013.01); *A61M 1/1601* (2014.02); *A61M 1/1641* (2014.02);
(Continued)

(58) Field of Classification Search
CPC ........ A61M 1/14; A61M 1/16; A61M 1/1601; A61M 1/1603; A61M 1/1621;
(Continued)

(56) References Cited

U.S. PATENT DOCUMENTS

| | | | | |
|---|---|---|---|---|
| 5,348,539 A * | 9/1994 | Herskowitz ......... | A61M 5/1483 604/141 |
| 5,634,896 A | 6/1997 | Bryant | |
| 2011/0186517 A1* | 8/2011 | Hedmann ........... | A61M 1/1656 210/103 |

FOREIGN PATENT DOCUMENTS

| | | |
|---|---|---|
| CN | 107837432 | 3/2018 |

OTHER PUBLICATIONS

International Search Report, PCT/US2021/046309 mailing date Nov. 16, 2021—3 pages.

(Continued)

*Primary Examiner* — Shefali D Patel
(74) *Attorney, Agent, or Firm* — K&L Gates LLP

(57) ABSTRACT

A peritoneal dialysis system includes a chamber; a hydraulic pump; an inflatable bladder located within the chamber and in hydraulic fluid communication with the hydraulic pump; and a control unit configured to cause a known amount of hydraulic fluid to be metered to the inflatable bladder and to determine (i) a first amount of air before a discharge stroke of the hydraulic pump via a first ideal gas law calculation, (ii) a second amount of air after the discharge stroke of the hydraulic pump via a second ideal gas law calculation, and (iii) a discharge volume of fresh or used dialysis fluid for the discharge stroke by subtracting a difference between the first amount of air and the second amount of air from the known amount of hydraulic fluid metered to the inflatable bladder for the discharge stroke.

25 Claims, 6 Drawing Sheets

(52) U.S. Cl.
CPC ............... *A61M 2205/3331* (2013.01); *A61M 2205/3379* (2013.01); *A61M 2210/1017* (2013.01)

(58) Field of Classification Search
CPC .............. A61M 1/1623; A61M 1/1631; A61M 1/1635; A61M 1/1639; A61M 1/1641; A61M 1/28; A61M 1/281; A61M 1/282; A61M 2205/33; A61M 2205/3327; A61M 2205/3331; A61M 2205/3379; A61M 2205/50; A61M 2210/1017
See application file for complete search history.

(56) References Cited

OTHER PUBLICATIONS

Written Opinion, PCT/US2021/046309 mailing date Nov. 16, 2021—11 pages.

* cited by examiner

PERITONEAL DIALYSIS SYSTEM USING PRESSURIZED CHAMBER AND PUMPING BLADDER

PRIORITY CLAIM

The present application claims priority to and the benefit of U.S. Provisional Application 63/067,006, filed Aug. 18, 2020, the entirety of which is herein incorporated by reference.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending upon the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

There is also a need for APD devices to be portable so that a patient may bring his or her device on vacation or for work travel.

For each of the above reasons, it is desirable to provide a relatively simple, compact APD machine, which operates a simple and cost effective disposable set.

SUMMARY

The present disclosure relates to an automated peritoneal dialysis ("APD") machine or cycler, which provides a chamber, which may be a plastic or metal rigid chamber. The chamber is reusable in one embodiment. A reusable inflatable bladder is located within the chamber. A source of motive fluid pressure, such as hydraulic pressure is fluidly connected to the chamber. The motive fluid is incompressible in one embodiment. The source of motive fluid is configured to deliver motive fluid to and remove motive fluid from the inflatable bladder. The source of motive fluid may include, for example, a syringe having a syringe plunger that is driven by a linear actuator.

The linear actuator may include, for example, a driver that is connected to the syringe plunger so as to be able to push and pull the plunger. The driver includes threads that thread onto a lead screw, ball screw or other type of rotational to translational conversion device. A motor is provided, which turns the lead or ball screw in a first direction to move the driver in a first direction and push the syringe plunger (to create positive pressure) and in a second direction to move the driver in an opposite, second direction to pull the syringe plunger (to create negative pressure). An encoder, e.g., mounted to the motor, may be provided to know how much the lead or ball screw has been turned and how much the driver and syringe plunger have been moved. A slide potentiometer or other position feedback device may be used instead of an encoder. A control unit is provided to control the motor and to receive signal outputs from the motor encoder. The signal outputs enable the control unit to know how much hydraulic fluid is contained in the inflatable bladder versus the syringe pump at all times.

In one embodiment, a pressure sensor is located along a line leading from the hydraulic, e.g., syringe pump, to the inflatable bladder. The pressure sensor outputs to the control unit, which monitors the hydraulic pressure. Because the hydraulic fluid, e.g., water or oil, is incompressible, the pressure measured represents the pressure of air within the reusable chamber. The measured pressure of air is used to determine the volume of fluid delivered in one embodiment.

A vent line is placed in fluid communication with the reusable chamber. A vent valve (e.g., pinch valve or pneumatic valve) under control of the control unit is provided to selectively open and close the vent valve to allow the inflatable bladder to vent air from within the chamber. A heater may also be provided to heat, under control of the control unit, dialysis fluid that has entered the chamber. At least a portion of the chamber may accordingly be thermally conductive or infrared transmissive to allow heat to be thermally or radiantly transmitted through the chamber portion to a fluid disposable located within the chamber.

In addition to the above-described reusable components, reusable pinch valves are provided to selectively open and close disposable fluid lines, such as a patient line, drain line and one or more solution lines. The pinch valves may be individually actuated, e.g., via electrically actuated solenoids under control of the control unit. Alternatively, one or more motor-driven cam under control of the control unit may be provided to place the fluid lines or tubes in a desired valve state.

Each of the reusable components described above is provided inside a housing in one embodiment. The housing may include a door that opens to remove a used disposable set and to receive a new disposable set. The housing may also include a display that provides information to the user or patient. The display cooperates with a touch screen overlay in one embodiment to provide a user interface for the user to enter commands into the control unit, which includes a video controller for operating the display.

The disposable set of the present system includes a flexible, inflatable container or bag sized to be inserted inside of the reusable chamber. The container or bag is connected to a single inlet/outlet tube in one embodiment. A sealing cap is sealed to the single inlet/outlet tube and is configured to seal the opening in the reusable chamber that receives the flexible, inflatable container or bag. The sealing cap may, for example, be sized to compress an o-ring provided at the opening of the reusable container.

The single inlet/outlet tube extends to a manifold that branches into multiple fluid lines or tubes, including a patient line or tube, a drain line or tube and one or more solution line or tube. If it is desired to provide a separate heating bag or inline heater, the manifold may further branch into a heating line or tube. In an embodiment, each of the multiple fluid lines or tubes branching off of the manifold line is located within a pinch valve or clamp upon loading the disposable set.

In an embodiment, the control unit is configured to use the ideal gas law to control a volume of used dialysis fluid removed from the patient and a volume of fresh dialysis fluid delivered to the patient. In a first step, the control unit opens the vent valve and at least one fluid line valve, such as a drain valve, and causes the hydraulic pump to apply positive pressure to the inflatable bladder to push as much air as possible out of the reusable chamber via the vent valve and out of the flexible container or bag via the at least one fluid line valve.

In a second step, with the vent valve closed and all fluid line valves closed except for a desired fluid source valve, e.g., patient line valve or solution line valve, the control unit causes the hydraulic pump to apply negative pressure to the inflatable bladder to retract the inflatable bladder, which creates a negative pressure in the flexible container or bag relative to atmospheric pressure, drawing a desired fluid, e.g., fresh or used dialysis fluid, into the flexible container or bag.

In a third step, with the vent valve closed and all fluid line valves closed, the control unit takes a first pressure measurement. The control unit then causes the hydraulic pump to pump a known amount of hydraulic fluid (e.g., using the motor encoder) into the inflatable bladder, which in turn compresses any air in chamber including any air in the flexible container or bag. The pressure sensor is next caused to measure and send to the control unit a second pressure measurement. The control unit then uses the difference between the first and second measured pressures, the change in volume within the chamber caused by the known volume injection of incompressible fluid into the chamber, and the ideal gas law ($PV=nRT$) to determine the volume of air within the reusable chamber (assuming no air in the inflatable bladder, and wherein the volume of air includes any air in the disposable container or bag and any air between the container and the chamber). The draw volume of fluid within the disposable container or bag is then determined to be the volume difference in hydraulic fluid volume before and after the draw stroke of the second step (measured, e.g., via the motor encoder) minus the determined volume of air (computed via the ideal gas law).

In a forth step, with the vent valve closed and all fluid line valves closed except for a desired fluid destination valve, e.g., patient line valve or drain line valve, the control unit causes the hydraulic pump to apply positive pressure to the inflatable bladder to expand the inflatable bladder, which creates a positive pressure in the flexible container or bag relative to atmospheric pressure, discharging a desired fluid, e.g., fresh or used dialysis fluid, from the flexible container or bag. If air resides within the container, at least some of it may be discharged as well.

In a fifth step, with the vent valve closed and all fluid line valves closed, the control unit takes a first pressure measurement. The control unit then causes the hydraulic pump to pump a known amount of hydraulic fluid (e.g., using the motor encoder) into the inflatable bladder, which in turn compresses any air in chamber including any air in the flexible container or bag. The pressure sensor is next caused to measure and send to the control unit a second pressure measurement. The control unit then uses the difference between the first and second measured pressures, the change in volume within the chamber caused by the known volume injection of incompressible fluid into the chamber, and the ideal gas law (PV=nRT) to determine the volume of air within the reusable chamber (assuming no air in the inflatable bladder, and wherein the volume of air includes any air in the disposable container or bag and any air between the container and the chamber). One or more temperature sensor may also be provided to account for any change in temperature, although temperature changes between pressure measurements are a minor contributor to the calculation.

The volume of fresh or used dialysis fluid discharged from the disposable container and chamber is then determined to be the difference in hydraulic fluid volume before and after the expel stroke of the fourth step (measured, e.g., via the motor encoder) less the difference in the computed volume of air (computed via the ideal gas law) in the third and fifth steps. That is, the difference in hydraulic fluid volume before and after the expel stroke of the fourth step corresponds to mostly fresh or used dialysis fluid being expelled from the chamber but also possibly a certain amount of air. To know the amount of air delivered, the amount of air in the container or bag and/or between the container and the chamber is measured before and after the expel stroke of the fourth step. Any difference is assumed to have been delivered along with the fresh or used dialysis fluid, the volume of which is determined by subtracting the air from the difference in hydraulic fluid.

If the computed volume of air is the same (no air is expelled or discharged), then the amount of dialysis fluid expelled or discharged is the same as the difference volume of hydraulic fluid before and after the expel stroke of the fourth step. The same is true if there is no air in the system.

Note that the volume of the chamber does not need to be known for determining either the draw volume or the discharge volume. It is instead required that the volume of the chamber does not change between making the first set of measurements before drawing or discharging dialysis fluid and the second set of measurements after drawing or discharging the dialysis fluid. The chamber is rigid in one embodiment so that its volume does not change.

The above steps are then repeated until a desired total patient fill or total patient drain volume (or condition) is met. At the end of treatment, the patient's ultrafiltration ("UF") may then be calculated by subtracting the total of all fill volumes from a total of all the drain volumes.

In light of the disclosure set forth herein, and without limiting the disclosure in any way, in a first aspect, which may be combined with any other aspect or portion thereof described herein, a peritoneal dialysis system includes: a chamber; a hydraulic pump; an inflatable bladder located within the chamber and in hydraulic fluid communication with the hydraulic pump; and a control unit configured to cause known amounts of hydraulic fluid to be metered to and from the inflatable bladder and to determine (i) a first amount of air before a discharge stroke via a first ideal gas law calculation, (ii) a second amount of air after the discharge stroke via a second ideal gas law calculation, and (iii) a discharge volume of fresh or used dialysis fluid for the discharge stroke by subtracting a difference between the first and second amounts of air from a known amount of hydraulic fluid metered to the inflatable bladder for the discharge stroke.

In a second aspect, which may be combined with any other aspect or portion thereof described herein, the peritoneal dialysis system includes a pressure sensor positioned and arranged to sense pneumatic pressure within the chamber, and wherein for (i) the control unit is further configured to (a) take a first pressure reading via the pressure sensor, (b) cause a first measurement amount of hydraulic fluid to be metered into the inflatable bladder and (c) take a second pressure reading via the pressure sensor for use with the first ideal gas law calculation, and wherein for (ii) the control unit is configured to (a) take a first pressure reading via the pressure sensor, (b) cause a second measurement amount of hydraulic fluid to be metered into the inflatable bladder and (c) take a second pressure reading via the pressure sensor for use with the second ideal gas law calculation.

In a third aspect, which may be combined with any other aspect or portion thereof described herein, the pressure sensor is positioned and arranged to sense pneumatic pressure within the chamber via sensing pressure of the hydraulic fluid acting as a pressure transmission medium.

In a fourth aspect, which may be combined with any other aspect or portion thereof described herein, the first and second measurement amounts of hydraulic fluid are at least substantially the same.

In a fifth aspect, which may be combined with any other aspect or portion thereof described herein, the control unit is further configured to determine a draw volume by subtracting the first amount of air before the discharge stroke from a known amount of hydraulic fluid metered from the inflatable bladder for a draw stroke.

In a sixth aspect, which may be combined with any other aspect or portion thereof described herein, the control unit is further configured to determine a volume of fresh or used dialysis fluid remaining in the chamber after the discharge stroke by subtracting the discharge volume from the draw volume.

In a seventh aspect, which may be combined with any other aspect or portion thereof described herein, the control unit is further configured to use the volume of fresh or used dialysis fluid remaining in the chamber for a repeat of (i) to (iii).

In an eighth aspect, which may be combined with any other aspect or portion thereof described herein, the peritoneal dialysis system includes a disposable set having a flexible container insertable within the chamber, the flexible container holding the discharge volume of fresh or used dialysis fluid.

In a ninth aspect, which may be combined with any other aspect or portion thereof described herein, the disposable set includes at least one fluid source line and at least one fluid destination line in fluid communication with the flexible container, and which includes a fluid source valve for each fluid source line and a fluid destination valve for each fluid destination line.

In a tenth aspect, which may be combined with any other aspect or portion thereof described herein, each of the fluid source valves and fluid destination valves is closed during (i) and (ii).

In an eleventh aspect, which may be combined with any other aspect or portion thereof described herein, the control unit is further configured to cause, prior to (i), one of the at least one source valves to be open and for the hydraulic pump to pull hydraulic fluid from the inflatable bladder to in turn pull fresh or used dialysis fluid into the flexible container in preparation for the discharge stroke.

In a twelfth aspect, which may be combined with any other aspect or portion thereof described herein, the control unit is further configured to cause, prior to (ii), one of the at least one destination valves to be open and for the hydraulic pump to push hydraulic fluid into the inflatable bladder to in turn push fresh or used dialysis fluid from the flexible container for the discharge stroke.

In a thirteenth aspect, which may be combined with any other aspect or portion thereof described herein, the hydraulic pump includes a syringe barrel and a syringe plunger.

In a fourteenth aspect, which may be combined with any other aspect or portion thereof described herein, the hydraulic pump includes a hydraulic fluid storage area, and wherein the hydraulic fluid is able to be metered back and forth between the hydraulic fluid storage area and the inflatable bladder.

In a fifteenth aspect, which may be combined with any other aspect or portion thereof described herein, the peritoneal dialysis system includes a linear actuator positioned and arranged to cause the hydraulic pump to meter the known amount of hydraulic fluid to and from the inflatable bladder.

In a sixteenth aspect, which may be combined with any other aspect or portion thereof described herein, the linear actuator includes a motor and a rotational to translational conversion device driven by the motor and in mechanical communication with the hydraulic pump.

In a seventeenth aspect, which may be combined with any other aspect or portion thereof described herein, the linear actuator includes a positional feedback device in operable communication with the control unit to provide positional feedback for the control unit to cause the known amount of hydraulic fluid to be metered to and from the inflatable bladder.

In an eighteenth aspect, which may be combined with any other aspect or portion thereof described herein, the peritoneal dialysis system includes a vent valve in pneumatic communication with the chamber, and wherein the control unit is further configured to cause the vent valve to open and the inflatable bladder to be filled with hydraulic fluid to vent air from the chamber prior to (i) to (iii).

In a nineteenth aspect, which may be combined with any other aspect or portion thereof described herein, the vent valve is closed during (i) to (iii).

In a twentieth aspect, which may be combined with any other aspect or portion thereof described herein, the control unit is configured to repeat (i) to (iii) until accumulated discharge volumes determined in (iii) meet a desired patient fill volume or a desired patient drain volume or until a drain condition is met.

In a twenty-first aspect, which may be combined with any other aspect or portion thereof described herein, a peritoneal dialysis system includes: a hydraulic pump including or operating with a hydraulic fluid storage area; a chamber; an inflatable bladder located within the chamber and in hydraulic fluid communication with the hydraulic pump; a disposable set including a flexible container insertable within the chamber; and a control unit configured to cause hydraulic fluid to be reuseably (i) pulled from the inflatable bladder into the hydraulic fluid storage area in a draw stroke in which fresh or used dialysis fluid is pulled into the flexible container and (ii) pushed from the hydraulic fluid storage area into the inflatable bladder in a discharge stroke in which fresh or used dialysis fluid is pushed from the flexible container.

In a twenty-second aspect, which may be combined with any other aspect or portion thereof described herein, the control unit is further configured to determine (i) a first amount of air before the discharge stroke via a first ideal gas law calculation, (ii) a second amount of air after the discharge stroke via a second ideal gas law calculation, and (iii) a discharge volume of fresh or used dialysis fluid for the discharge stroke by subtracting a difference between the first and second amounts of air from a known amount of hydraulic fluid pushed to the inflatable bladder for the discharge stroke.

In a twenty-third aspect, which may be combined with any other aspect or portion thereof described herein, a peritoneal dialysis system includes: a hydraulic pump; a chamber; an inflatable bladder located within the chamber and in hydraulic fluid communication with the hydraulic pump; and a control unit configured to cause (i) a draw stroke in which a measured amount of hydraulic fluid is removed from the inflatable bladder to draw fresh or used dialysis fluid into the chamber, (ii) a first air amount determination to be made by taking pressure measurements before and after attempting to compress air within the chamber, (iii) a discharge stroke in which a measured amount of hydraulic fluid is delivered to the inflatable bladder to discharge fresh or used dialysis fluid from the chamber, (iv) a second air amount determination to be made by taking pressure measurements before and after attempting to compress air within the chamber and the flexible container, and (v) a discharge volume of fresh or used dialysis fluid for the discharge stroke to be determined by subtracting a difference between the first and second air amounts from the measured amount of hydraulic fluid delivered to the inflatable bladder for the discharge stroke.

In a twenty-fourth aspect, which may be combined with any other aspect or portion thereof described herein, the peritoneal dialysis system includes a flexible container located within the chamber, the flexible container holding the fresh or used dialysis fluid, and wherein in (ii) and (iv) attempting to compress air includes attempting to compress air within the flexible container and between the flexible container and the chamber.

In a twenty-fifth aspect, which may be combined with any other aspect or portion thereof described herein, attempting to compress air within the chamber includes delivering hydraulic fluid to the inflatable bladder.

In a twenty-sixth aspect, which may be combined with any other aspect or portion thereof described herein, the control unit is further configured to cause a draw volume of fresh or used dialysis fluid in the chamber to be determined by subtracting the first air amount from the measured amount of hydraulic fluid removed from the inflatable bladder.

In a twenty-seventh aspect, which may be combined with any other aspect or portion thereof described herein, the control unit is configured to repeat (i) to (v) until a desired patient fill volume or a desired patient drain volume or drain condition is met.

In a twenty-eighth aspect, which may be combined with any other aspect or portion thereof described herein, the first and second air amount determinations are performed using an ideal gas law evaluation of the pressure measurements taken before and after attempting to compress air within the chamber.

In a twenty-ninth aspect, any of the features, functionality and alternatives described in connection with any one or more of FIGS. 1 to 10 may be combined with any of the features, functionality and alternatives described in connection with any other of FIGS. 1 to 10.

It is accordingly an advantage of the present disclosure to provide a relatively volumetrically accurate automated peritoneal dialysis ("APD") cycler.

It is another advantage of the present disclosure to provide an APD cycler that achieves relatively precise pressure control.

It is a further advantage of the present disclosure to provide a relatively quiet APD cycler.

It is still another advantage of the present disclosure to provide an APD cycler that is safe regarding the infusion of the patient with air.

It is yet a further advantage of the present disclosure to provide an APD system that may use a same disposable item for both pumping and heating.

It is still a further advantage of the present disclosure to provide an APD system that is able to build motive fluid or pumping pressure in a relatively simple manner.

It is yet another advantage of the present disclosure to provide an APD system that employs a relatively low cost disposable set.

Still further, it is an advantage of the present disclosure to provide an APD system that is capable of pumping a high flowrate using a relatively small disposable.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
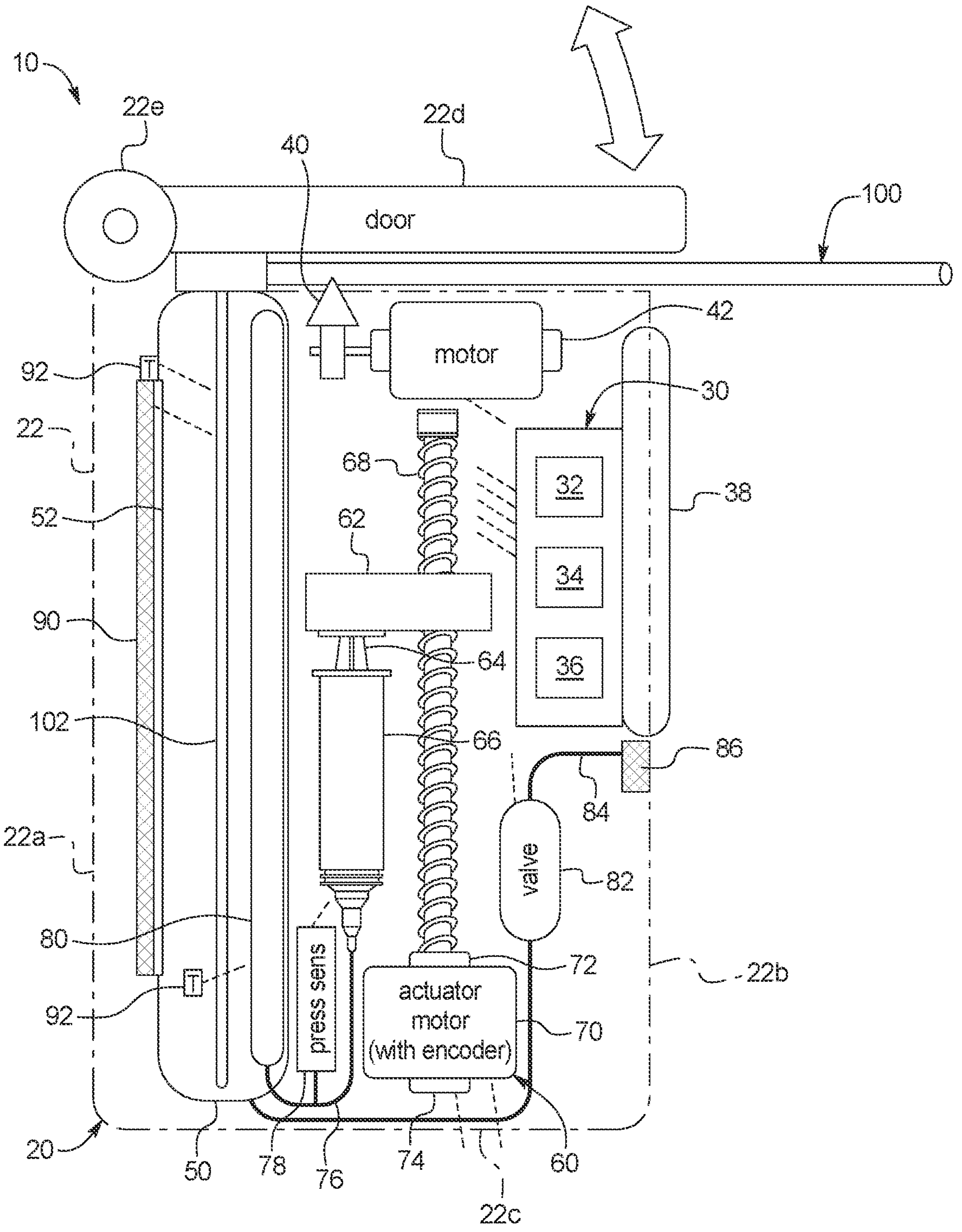
FIG. 1 is a schematic view of one embodiment of an automated peritoneal dialysis ("APD") cycler using a reusable chamber and inflatable bladder of the present disclosure.

Referring now to the drawings and in particular to FIG. 1, an automated peritoneal dialysis ("APD") system 10 includes and APD machine or cycler 20 that operates with a disposable set 100. APD machine or cycler 20 includes a housing 22 that holds a reusable chamber 50. Housing 20 and chamber 50 in the illustrated embodiment are both rigid structures, which may be made of plastic, such as, polyvinyl chloride ("PVC"), polyethylene ("PE") or polyurethane ("PU"), or of metal, such as stainless steel or aluminum. Housing and chamber 50 are each reusable in one embodiment.

Reusable chamber 50 accepts a disposable container or bag 102 of disposable set 100, such as a disposable flexible container or bag. Disposable container or bag 102 and the associated tubing of disposable set 100 may be made of a medically safe material such as PVC or a non-PVC material.

Housing 22 as illustrated in FIG. 1 includes sidewalls 22*a*, 22*b*, etc., a bottom wall 22*c* and a door or lid 22*d* that is hinged via a hinge 22*e* to one of the sidewalls, e.g., sidewall 22*a*. Door 22*d* hinges open to accept flexible container or bag 102. One advantageous aspect of APD system 10 is that it is not critical how flexible container or bag 102 fits inside reusable chamber 50. The user simply slides flexible container 102 into a slot formed within reusable chamber 50, as illustrated in more detail below, and then closes door 22*d* for operation.

Housing 22 houses a linear actuator 60. Linear actuator 60 in the illustrated embodiment includes a driver 62 that is connected to a syringe plunger 64 so as to be able to push and pull the plunger. Syringe plunger 64 is fitted moveably and sealingly within a syringe barrel 66. Plunger 64 and barrel 66 form a hydraulic pump discussed in more detail below. It should be appreciated however that a different type of hydraulic pump may be used, e.g., a piston or membrane pump. In an embodiment, the piston or membrane pump, like the present syringe pump, is able to deliver a known amount of hydraulic fluid to, and remove a known amount of hydraulic fluid from, reusable chamber 50. In an embodiment, each variation of the hydraulic pump has or is in fluid communication with a hydraulic fluid storage area (syringe barrel 66 in the illustrated embodiment) that allows hydraulic fluid to be reused back and forth between the storage area and reusable chamber 50.

Driver 62 includes internal female threads that thread onto the male threads of a lead or ball screw 68. A motor 70, such as a stepper motor or AC or DC servo motor, is provided, which is coupled to lead or ball screw 68 via a coupler 72, e.g., an anti-backlash coupler that increases overall accuracy. Motor 70 turns lead or ball screw 68 in a first direction to move driver 62 in a first direction and push syringe plunger 64 within syringe barrel 66 (to create positive pressure) and in a second direction to move driver 62 in an opposite, second direction to pull syringe plunger 64 within syringe barrel 66 (to create negative pressure). An encoder 74, e.g., mounted to the motor, may be provided to know how much lead or ball screw 68 has been turned and how much driver 62 and syringe plunger 64 have been moved. Knowing the amount of movement and the constant cross-sectional area of syringe barrel 66 enable a known amount of hydraulic fluid to be metered to and removed from reusable chamber 50.

A reusable inflatable bladder 80 is located inside reusable chamber 50. Bladder 80 is in hydraulic communication with syringe barrel via a hydraulic line 76. Inflatable bladder 80 may be made of any of the materials discussed herein and may alternatively be made of silicone rubber. A pressure sensor 78 is positioned along hydraulic line so as to sense the pressure of the hydraulic fluid, e.g., water or oil, driven by the hydraulic pump, e.g., syringe plunger 64 and syringe barrel 66. The pressure of fresh dialysis fluid delivered to the patient and used dialysis fluid removed from the patient is therefore known and controllable using feedback from pressure sensor 74. Additionally, when syringe plunger 64 and syringe barrel 66 are at rest and not being actuated, the incompressible hydraulic fluid provides a pressure transmission medium that transfers the pressure or air within reusable chamber 50 to pressure sensor 78. System 10 accordingly knows the at-rest air pressure within chamber 50.

FIG. 1 further illustrates a reusable vent valve 82 located along a vent line 84, which is in pneumatic communication with known volume and reusable chamber 50. Vent valve 82 is opened at selective times discussed herein to allow the hydraulic pump, e.g., syringe plunger 64 and syringe barrel 66, to fully inflate bladder 80 within chamber 50 to vent air from the chamber via vent line 84. Vent valve 84 may be an electromechanically actuated pinch valve or be a pneumatic valve as desired. If needed, a filter 86 such as a hydrophobic filter may be placed at the end of vent line 84.

In addition to the above-described reusable components, reusable pinch valves are provided to selectively open and close disposable fluid lines, such as a patient line, drain line and one or more solution lines discussed herein. The pinch valves may be individually actuated, e.g., via electrically actuated solenoids under control of the control unit. Alternatively, one or more cam 40 driven by a motor 42 may be provided to place the fluid lines or tubes in a desired valve state.

FIG. 1 further illustrates that cycler 20 of system 10 may include a heater 90 positioned adjacent to reusable chamber 50 and one or more temperature sensor 92 positioned and arranged to sense at temperature inside chamber 50 and/or a temperature of adjacent surface 52 of chamber 50. It should be appreciated that the one or more temperature sensor 92 may be provided even if heater 90 is not provided, e.g., placed so as to contact container or bag 102 to sense the temperature of fresh or used dialysis fluid held therein. The output of temperature sensor 92 in any case may also be used in the ideal gas law calculations discussed herein, namely, for any change in temperature T in PV=nRT. Heater may be any one or more of a resistive plate heater, an infrared heater and/or an inductive heater. If heater 90 is or includes an infrared heater, surface 52 may be made of an infrared transmitting material, such as quartz glass. If heater 90 is or includes a resistive plate heater, surface 52 may be made of a thermally conductive material, such as stainless steel, aluminum and/or copper. Heater 90 is actuated so as to heat fluid within container or bag 102 to body temperature, e.g., 37° C.

In the illustrated embodiment of FIG. 1, APD machine or cycler 20 of system 10 includes a control unit 30. Control unit 30 is alternatively or additionally provided as a wireless user interface, such as a tablet or smartphone. In any case, as illustrated in FIG. 1, control unit 30 may include one or more processor 32, one or more memory 34, and a video controller 36 interfacing with a user interface 38, which may include a display screen (e.g., provided along the side 22*d* of housing 22) operating with a touchscreen and/or one or more electromechanical button, such as a membrane switch. User interface 38 may also include one or more speaker for outputting alarms, alerts and/or voice guidance commands. Control unit 30 may also include a transceiver and a wired or wireless connection to a network, e.g., the internet, for sending treatment data to and receiving prescription instructions from a doctor's or clinician's server interfacing with a doctor's or clinician's computer.

Control unit 30 is programmed control hydraulic pump motor 60 and to receive signal outputs from motor encoder 74. The signal outputs enable control unit 30 to know how much hydraulic fluid is contained in inflatable bladder 80 versus syringe barrel 66 at all times. Control unit 30 receives pressure signals from pressure sensor 78 to control dialysis fluid pumping pressure and to know the air pressure within known volume chamber 50 for the ideal gas law volume calculations discussed herein. Control unit 30 is also programmed to control the pinch valves or the valve lobes of cam 40 driven by motor 42 as discussed herein to direct fluid as needed. Control unit 30 is further programmed to control vent valve 82 (pneumatically or electromechanically) to vent air from chamber 50 when desired. Further still, control unit operates heater 90 as needed to heat fresh dialysis fluid to, e.g., body temperature of 37° C. via feedback from one or more temperature sensor 92 inputted into a heater algorithm, such as a proportional, integral and derivative ("PID") algorithm.

Figure 2:
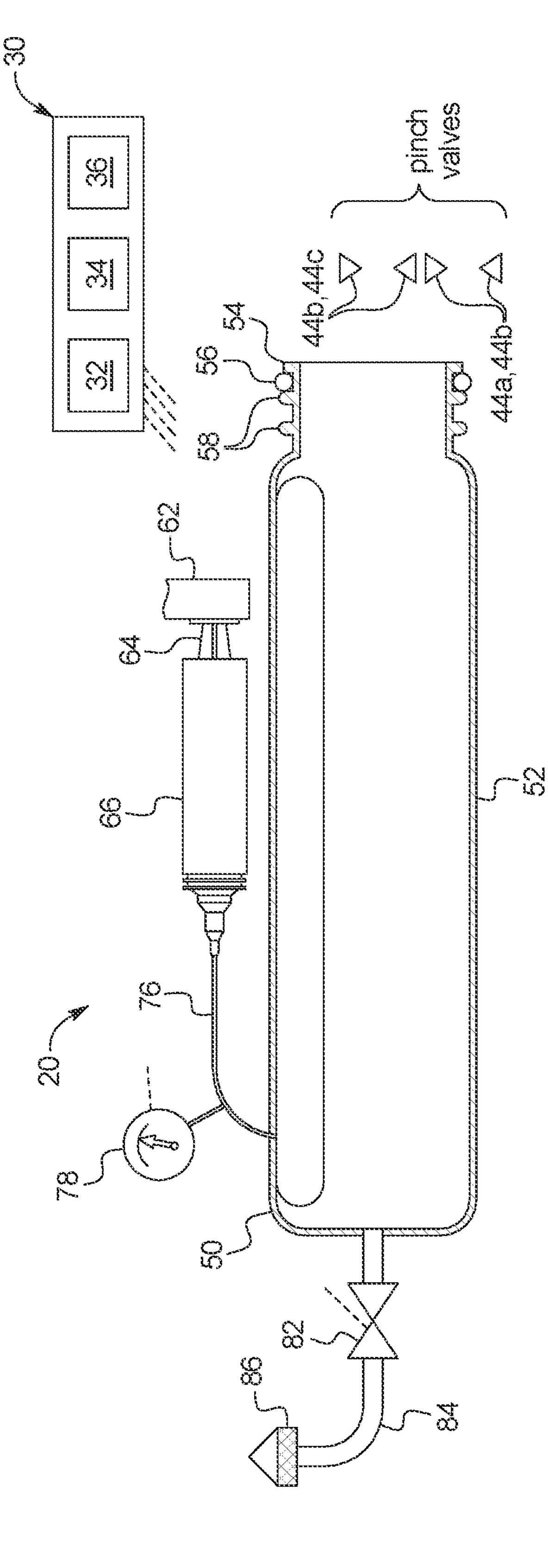
FIG. 2 is side-sectioned view of one embodiment of a reusable chamber and associated reusable equipment of the APD cycler of the present disclosure.

Referring now to FIG. 2, the hydraulic pump, e.g., syringe plunger 64 and syringe barrel 66, known volume container 50, pressure sensor 78, and vent valve 82 in more detail. Pressure sensor 78 is located along or operable with hydraulic line 76 extending between syringe barrel 66 and inflatable bladder 80. Vent valve 82 is located along vent line 84, which may lead to protective air filter 86. Pressure sensor 78 outputs to control unit 30, while vent valve is under control of control unit as illustrated by the dashed lines leading from the sensor and valve.

FIG. 2 further illustrates that a pinch valves 44*a*, 44*b*, 44*c* are provided for each line of disposable set 100. As discussed in connection with FIG. 1, the pinch valves may in one embodiment be provided by one or more cam 40 driven by a motor 42. FIG. 2 illustrates that source pinch valves 44*b*, 44*c* and destination pinch valves 44*a*, 44*b* may alternatively be provided with integrated solenoids that are, in one fail safe embodiment, energized open and deenergized closed. Patient line pinch valve 44*b* is at different times a source and a destination pinch valve.

FIG. 2 illustrates surface 52 of chamber 50, which is placed in contact with or adjacent to heater 90 as illustrated in connection with FIG. 1. Reusable chamber 50 also includes a sealing surface 54. Sealing surface 54 in the illustrated embodiment includes a collar that holds a reusable o-ring 56, such as a compressible silicone o-ring. O-ring 56 is compressed when container or bag 102 is placed inside known volume chamber 50 to provide a sealed environment inside the chamber. The collar also includes snap-fitting outwardly projecting protrusions 58, which operate with a mating disposable protrusion when container or bag 102 is placed inside known volume chamber 50 to prevent container or bag 102 from disengaging with chamber 50 when the chamber is placed under positive pressure.

Figure 3:
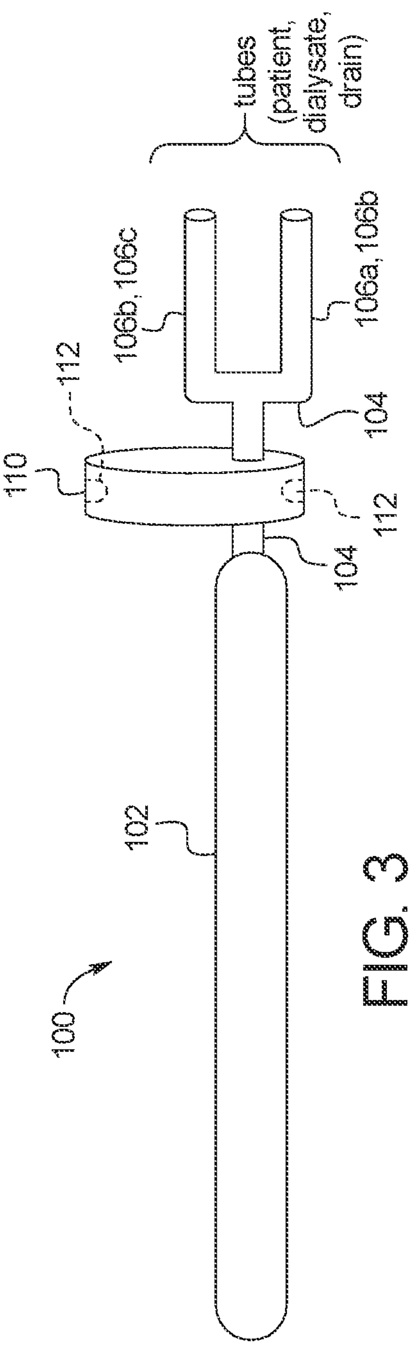
FIG. 3 is a side view of one embodiment of a portion of a disposable set of the present disclosure.

FIG. 3 illustrates a portion of disposable set 100 in more detail. Disposable set 100 includes container or bag 102 that communicates fluidly with a manifold line 104. Manifold line 104 in FIG. 3 splits into fluid source lines 106*b*, 106*c* and fluid destination lines 106*a*, 106*b*. Patient line 106*b* is at different times a fluid source line and a fluid destination line.

Disposable set 100 includes a rigid cap 110 located along and sealed to manifold line 104, and which may be made of any of the materials discussed herein. Cap 110 includes an internal radius sized to compress reusable o-ring 56 when cap 110 is inserted over the collar of sealing surface 54. Cap 110 additionally incudes an inwardly projecting, snap-fitting protrusion 112 that engages reusable outwardly projecting protrusions 58 of sealing surface 54. The structure allows the user or patient to readily translate flexible container or bag 102 into and out of reusable chamber 50 and in the process seal and lock and unseal and unlock cap 110 to and from sealing surface 54.

Figure 4C:
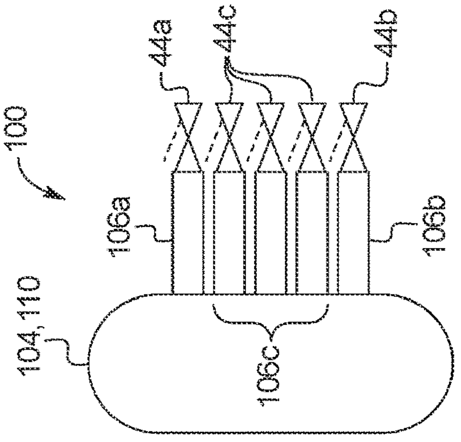
FIGS. 4A to 4C are top, side and edge views, respectively, of one embodiment of a portion of a disposable set of the present disclosure.
Figure 4A:
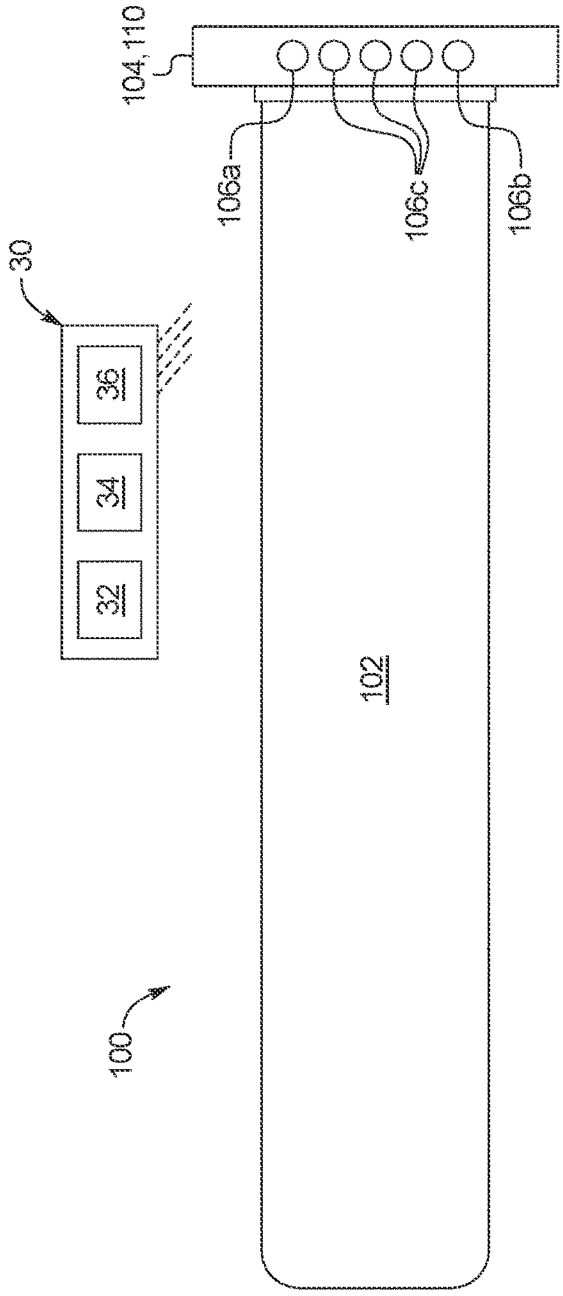
Figure 4B:
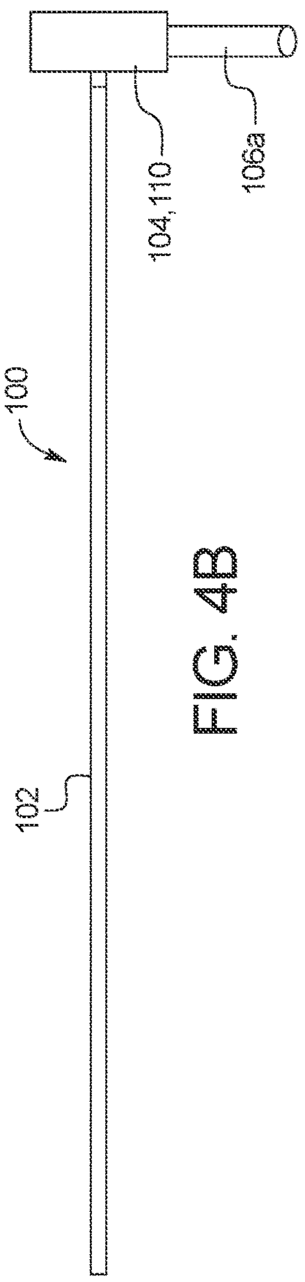

FIGS. 4A to 4C illustrate disposable set 100, and in particular container or bag 102, from different views. FIG. 4A illustrates the wide side of container or bag 102 extending from manifold and cap 110. The dimension of the wide side in FIG. 4A along with the length primarily sets the volume of fluid held within container or bag 102. In an embodiment, container or bag 102 holds anywhere, between and including, 20 ml to 500 ml liters of fresh or used dialysis fluid, e.g., 200 ml. Bag or container may accordingly be filled and emptied anywhere, and including, four (two liter fill at 500 ml volume) to one-hundred-fifty (three liter drain at 20 ml volume) times over an entire patient fill or drain, e.g., over a two liter patient fill or over a three liter patient drain.

FIG. 4B illustrates that the edge or thin side of container or bag 102 is relatively thin, allowing the corresponding dimension of reusable chamber 50 to also be thin. The overall APD cycler 20 of system 10 may accordingly be termed a slot cycler or slot pump because loading container or bag 102 for operation is largely an act of sliding the container or bag into its dedicated slot.

FIG. 4C illustrates manifold or manifold line 104 and cap 110 from the top, where the patient or user is looking down while inserting container or bag 102 into or removing container or bag 102 from reusable chamber 50. Lines 106*a* to 106*c* are illustrated extending from manifold or manifold line 104 and cap 110, and which are respectively in operable communication with pinch valves 44*a* to 44*c*. In the illustrated embodiment, disposable set 100 includes five lines, e.g., drain line 106*a*, patient line 106*b* and three solution lines 106*c*. More or less than three solutions may be provided. Although not illustrated, disposable set 100 also includes solution bags, such as bags holding dextrose-based PD solution and a last bag PD fluid, e.g., icodextrin. In an alternative embodiment, system 10 and disposable set 100 are configured for operation with an online source of PD fluid. In a further alternative embodiment, disposable set 100 includes one or more batch or inline fluid heating line.

FIGS. 5 to 10 illustrate one embodiment for operating system 10 of the present disclosure, which is stored on one or more memory 34 and is operated by one or more processor 32 of control unit 30. As described herein, control unit 30 is configured to use the ideal gas law to determine a volume of used dialysis fluid removed from the patient and a volume of fresh dialysis fluid delivered to the patient. In each of FIGS. 5 to 10, flexible container or bag 102 has been inserted into known volume chamber 50 and cap 110 has been releasably sealed and pressure locked to sealing surface 54.

Figure 5:
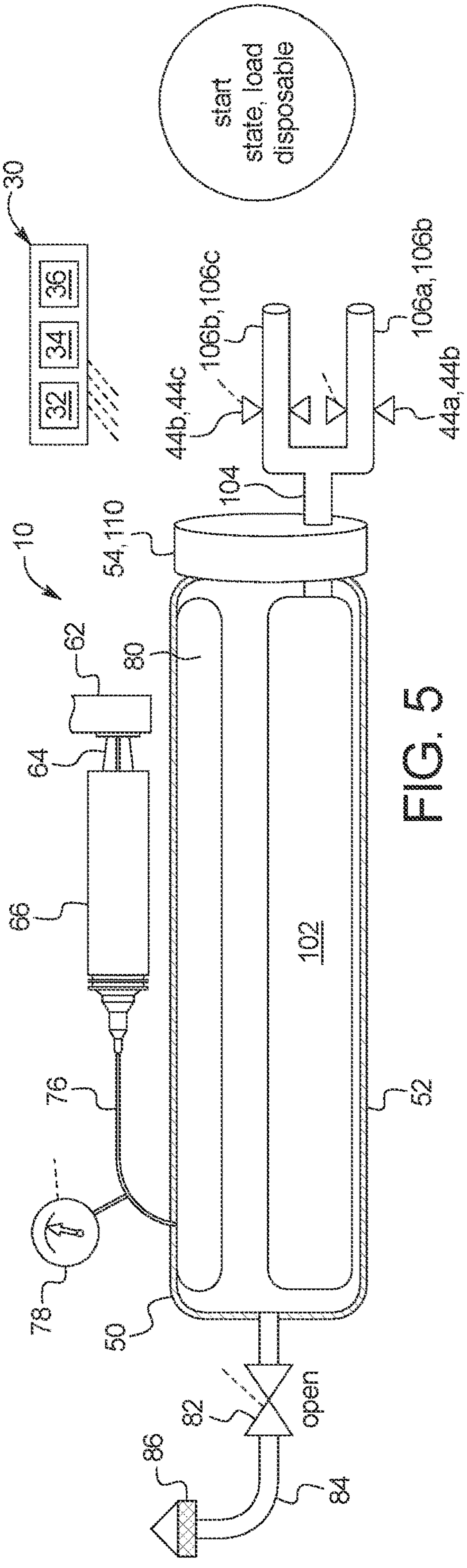
FIG. 5 is a side view of one embodiment of the present disclosure for the flexible container or bag loaded into the reusable chamber, the container and chamber in an idle state.

FIG. 5 illustrates an idle state in which vent valve 82 is opened or closed, pinch valves 44*a* to 44*c* are opened or closed, while hydraulic pump, e.g., syringe plunger 64, and syringe barrel 66, is not operated. Pressure sensor 78 outputting to control unit 30 may read zero psig.

Figure 6:
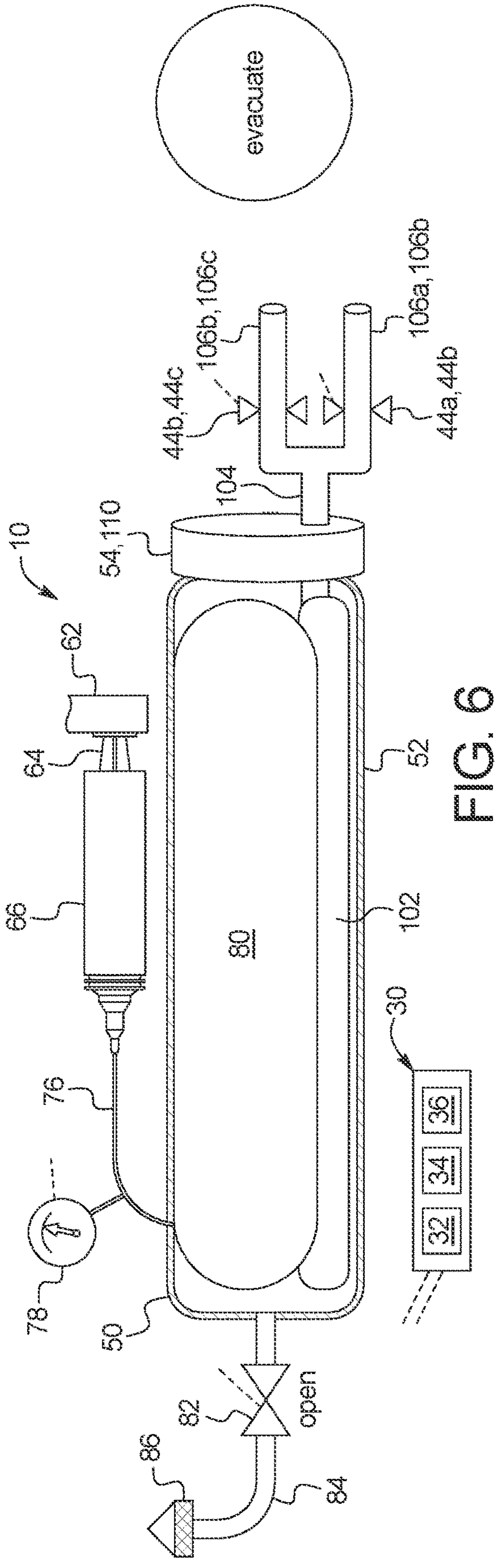
FIG. 6 is a side view of one embodiment of the present disclosure for the flexible container or bag loaded into the reusable chamber, the container and chamber in a vent state.

FIG. 6 illustrates that in a first, vent step for operating APD system 10, control unit 30 causes vent valve 82 and at least one fluid line valve 44*a* to 44*c*, such as a drain line valve 44*a*, to be opened, and causes the hydraulic pump 64, 66 to apply positive incompressible fluid pressure to inflatable bladder 80 to in turn push as much air (and possibly fresh or used dialysis fluid) as possible out of the reusable chamber 50 via vent valve 82 and out of flexible container or bag 102 via at least one fluid line valve 44*a* to 44*c*. The positive pressure applied during the vent step, as measured by pressure sensor 78 outputting to control unit 30, is not patient sensitive and may therefore be controlled to be a maximum safe pressure for inflatable bladder 80, reusable chamber 50 and flexible container or bag 102, e.g., eight psig, to minimize venting time.

Pressure control for each operation step of system 10 discussed herein may be accomplished by delivering a designated (e.g., via a look-up table stored in one or more memory 34) electrical current to motor 70 for linear actuator 60. Control unit 30 accordingly includes one or more motor driver or controller in communication with processor 32 and memory 34 for executing such electrical current control.

In the first step of FIG. 6, control unit 30 knows the amount of hydraulic fluid delivered to inflatable bladder 80 for venting via feedback from motor encoder 74.

Figure 7:
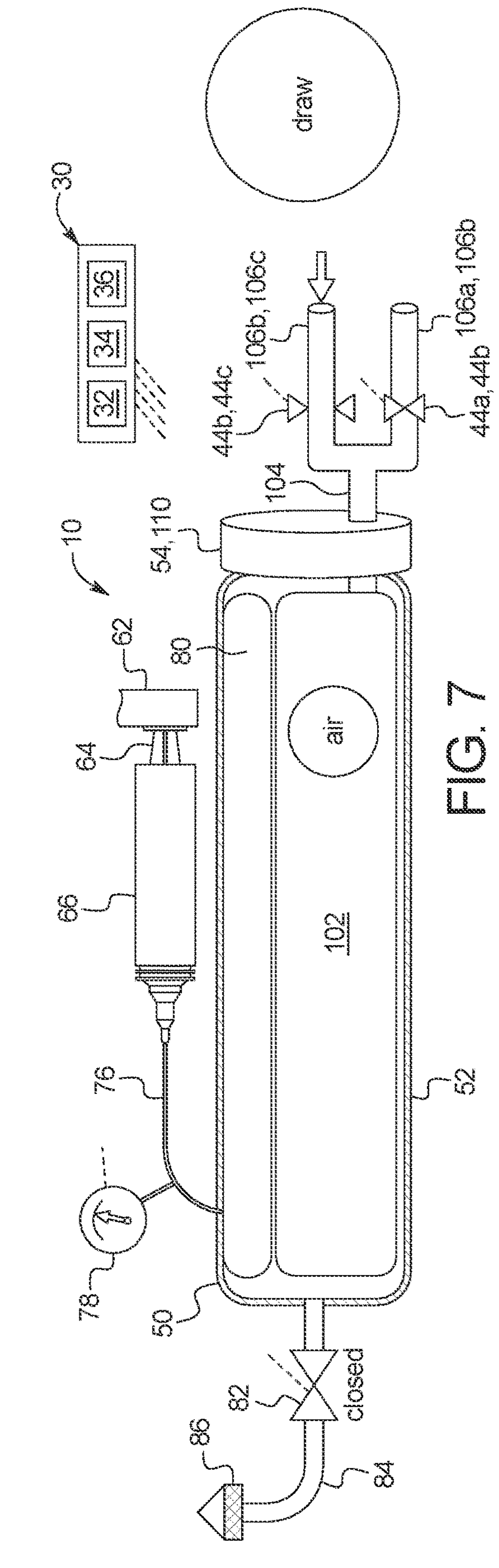
FIG. 7 is a side view of one embodiment of the present disclosure for the flexible container or bag loaded into the reusable chamber, the container and chamber in a draw state.

FIG. 7 illustrates that in a second, draw step for operating APD system 10, control unit 30 causes vent valve 82 to be closed and all fluid line valves to be closed except for a desired fluid source valve 44*b*, 44*c*, e.g., patient line valve 44*b* or solution line valve 44*c*. Control unit 30 also causes hydraulic pump 64, 66 to apply negative incompressible hydraulic fluid pressure to inflatable bladder 80 to retract the inflatable bladder, which creates a corresponding negative pressure in flexible container or bag 102 relative to atmospheric pressure, drawing a desired fluid, e.g., fresh or used dialysis fluid, into the flexible container or bag.

The applied negative pressure, as measured by pressure sensor 78 outputting to control unit 30, is patient sensitive if pulling used dialysis fluid from the patient and is therefore controlled to be at or within a safe drain pressure limit, e.g., −1.5 psig to −3.0 psig. The applied negative pressure, as measured by pressure sensor 78 outputting to control unit 30, is not patient sensitive if pulling fresh dialysis fluid from a solution container and is therefore controlled to be within a safe pressure limit for inflatable bladder 80, reusable chamber 50 and flexible container or bag 102, e.g., −5 psig to 8 psig, to minimize solution draw time into container or bag 102.

In the second step of FIG. 7, control unit 30 knows the amount of hydraulic fluid removed from inflatable bladder 80 for the fresh or used dialysis fluid draw via feedback from motor encoder 74. What is not known is how much air, if any, has been drawn in with fresh or used dialysis fluid.

Figure 8:
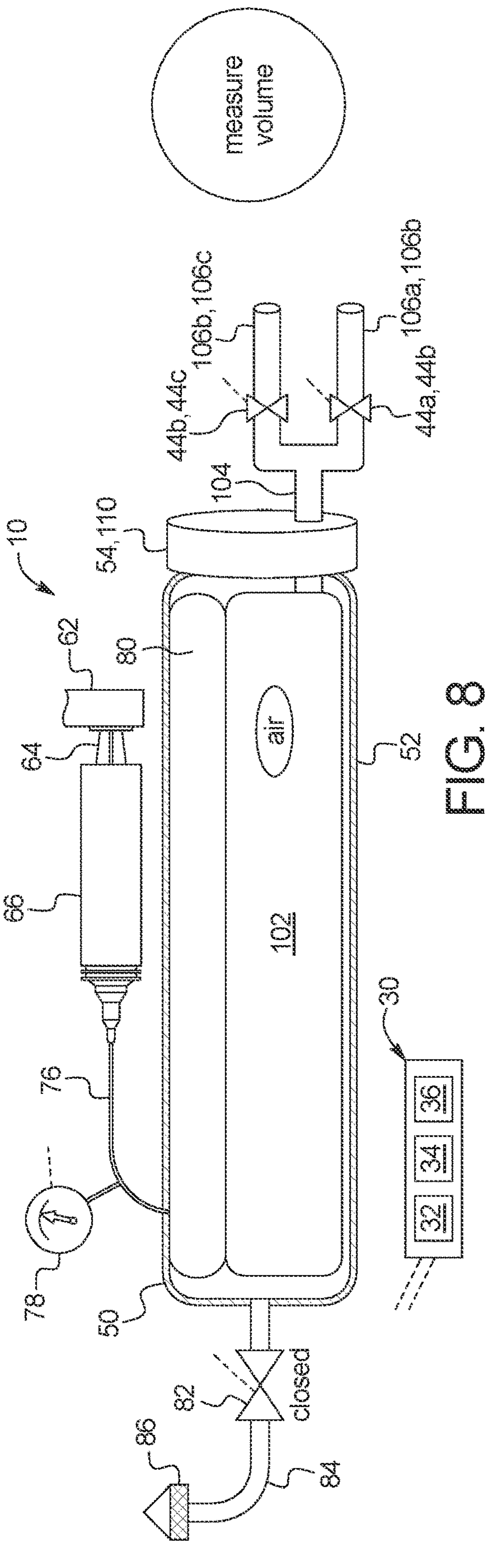
FIG. 8 is a side view of one embodiment of the present disclosure for the flexible container or bag loaded into the reusable chamber, the container and chamber in a first pressure measurement state.

FIG. 8 illustrates that in a third, volume calculation step for operating APD system 10, control unit 30 causes vent valve 82 to remain closed and for all fluid line valves 44*a* to 44*c* to be closed. Control unit 30 takes a first pressure measurement via pressure sensor 78. Control unit 30 then causes hydraulic pump 64, 66 to pump a known amount of hydraulic fluid (e.g., using feedback from motor encoder 74) into inflatable bladder 80, which in turn compresses any air in chamber 50, including any air in flexible container or bag 102. In an embodiment, the known amount of hydraulic fluid pumped is about 10 ml to 15 ml. Control unit 30 next takes a second pressure measurement using pressure sensor 78. Control unit 30 then uses the difference between the first and second measured pressures, the known volume change caused by the, e.g. 10 to 15 ml of incompressible fluid delivered into chamber 50, and the ideal gas law (PV=nRT) to determine the volume of air within reusable chamber 50 (assuming no air resides in inflatable bladder 80, and wherein the volume of air includes any air in disposable container or bag 102 as well as any air between container 102 and chamber 50).

The draw volume of fluid within disposable container or bag 102 is then determined to be the volume difference in hydraulic fluid volume before and after the draw stroke of the second step of FIG. 7 (measured, e.g., via the motor encoder) minus the volume of air determined in connection with FIG. 8 (computed via the ideal gas law).

Figure 9:
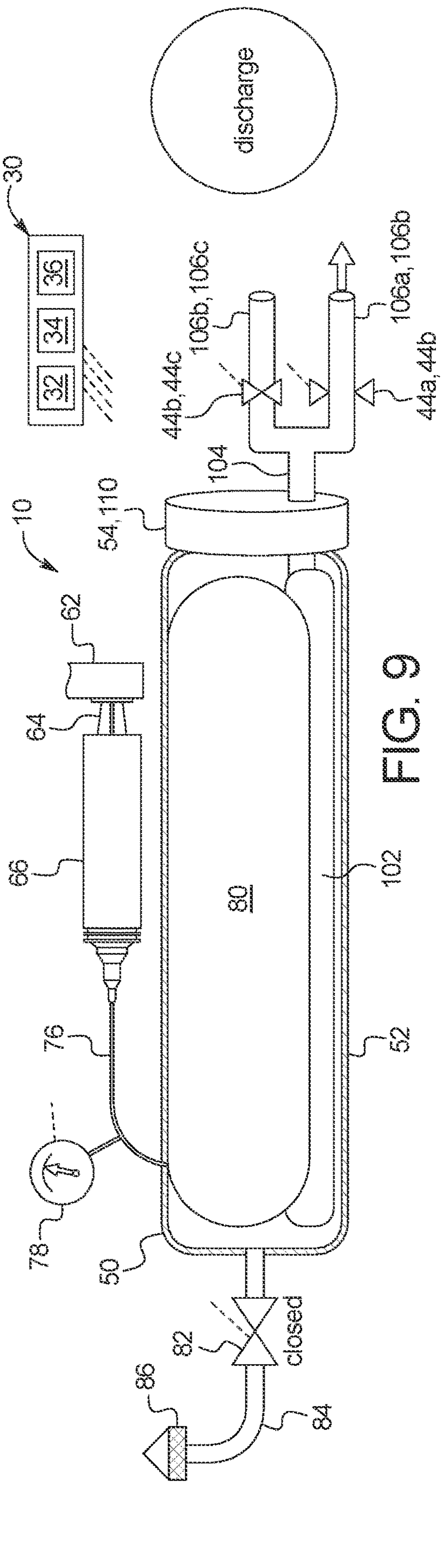
FIG. 9 is a side view of one embodiment of the present disclosure for the flexible container or bag loaded into the reusable chamber, the container and chamber in a discharge state.

FIG. 9 illustrates that in a fourth, fluid discharging step for operating APD system 10, control unit 30 causes vent valve 82 to remain closed and all fluid line valves to be closed except for a desired fluid destination valve 44*a*, 44*b*, e.g., patient line valve 44*b* or drain line valve 44*a*. Control unit 30 causes hydraulic pump 64, 66 to apply positive pressure to inflatable bladder 80 to expand the inflatable bladder, which in turn creates a positive pressure in flexible container or bag 102 relative to atmospheric pressure, discharging a desired amount of a desired fluid, e.g., fresh or used dialysis fluid, from the flexible container or bag. An amount of air inside flexible container or bag 102 may also be discharged and is a variable.

The applied positive pressure, as measured by pressure sensor 78 outputting to control unit 30, is patient sensitive if pushing fresh dialysis fluid to the patient and is therefore controlled to be within a safe patient fill pressure limit, e.g., +3.0 psig to +5.0 psig. The applied positive pressure, as measured by pressure sensor 78 outputting to control unit 30, is not patient sensitive if pushing used dialysis fluid to drain and is therefore controlled to be within a safe pressure limit for inflatable bladder 80, reusable chamber 50 and flexible container or bag 102, e.g., eight psig, to minimize discharging time from container or bag 102.

In the fourth step of FIG. 9, control unit 30 knows the amount of hydraulic fluid delivered to inflatable bladder 80 for fresh or used dialysis fluid discharging via feedback from motor encoder 74.

Figure 10:
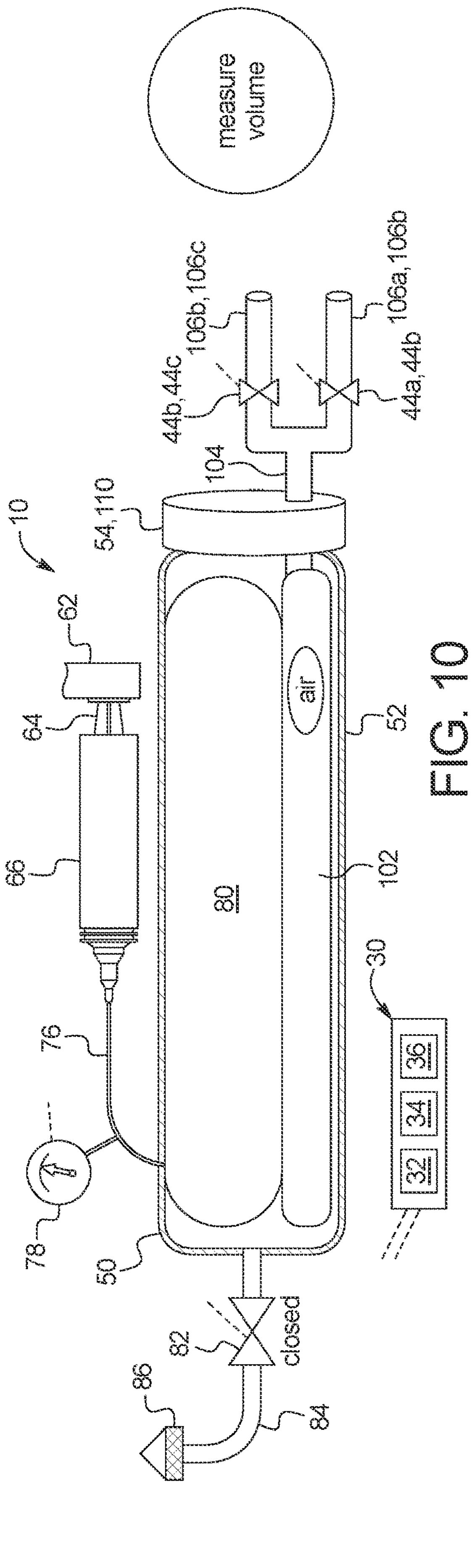
FIG. 10 is a side view of one embodiment of the present disclosure for the flexible container or bag loaded into the reusable chamber, the container and chamber in a second pressure measurement state.

FIG. 10 illustrates that in a fifth, volume calculation step for operating APD system 10, control unit 30 causes vent valve 82 to remain closed and for all fluid line valves 44*a* to 44*c* to be closed. Control unit 30 takes a first pressure measurement via pressure sensor 78. Control unit 30 then causes hydraulic pump 64, 66 to pump a known amount of hydraulic fluid (e.g., using feedback from motor encoder 74) into inflatable bladder 80, which in turn compresses any air in chamber 50, including any air in flexible container or bag 102. In an embodiment, the known amount of hydraulic fluid pumped may again be about 10 ml to 15 ml. Control unit 30 next takes a second pressure measurement using pressure sensor 78. Control unit 30 then uses the difference between the first and second measured pressures, the known volume change caused by the, e.g. 10 to 15 ml of incompressible fluid delivered into chamber 50, and the ideal gas law (PV=nRT) to determine the volume of air within reusable chamber 50 (assuming no air resides in inflatable bladder 80, and wherein the volume of air includes any air in disposable container or bag 102 as well as any air between container 102 and chamber 50).

The volume of fresh or used dialysis fluid discharged from container or bag 102 and chamber 50 is then determined to be the known volume hydraulic fluid delivered to inflatable bladder 80 in the fourth step of FIG. 9 less the difference in the amount of air determined in FIGS. 8 and 10, which is the amount of air that is pumped out of chamber 50 along with fresh or used dialysis fluid in FIG. 9. If the computed volume of air is the same in FIGS. 8 and 10 (no air is expelled or discharged), then the amount of dialysis fluid expelled or discharged in the fourth step of FIG. 9 is the same as the volume difference of hydraulic fluid before and after the expel stroke of the fourth step of FIG. 9. The same is true if there is no air in the container or bag 102 or between container 102 and chamber 50.

Note that the volume of the chamber 50 does not need to be known for determining either the draw volume or the discharge volume. It is instead required that the volume of chamber 50 does not change between making the first set of measurements before drawing or discharging dialysis fluid and the second set of measurements after drawing or discharging the dialysis fluid. Chamber 50 is rigid in one embodiment so that its volume does not change.

It should also be noted that for both pressure measurement steps of FIGS. 8 and 10, if there is no air (or very little air) in container 102 or between container 102 and chamber 50, moving very small volumes of hydraulic fluid into inflatable bladder 80 will spike the pressure measured pressure sensor 78, which is easy for control unit 30 to detect. In such a situation, and in the other situation in which no air is expelled and the volume difference of the hydraulic fluid corresponds directly to the volume difference of dialysis fluid, the ideal gas law does not need to be used. It is accordingly expressly contemplated for control unit 30 to look for a pressure spike in the likely case that there is little to no air in chamber 50 or container 102.

The first to fifth steps listed above are then repeated in one embodiment until a desired total patient fill volume or a desired total patient drain volume (or condition) is met, e.g., as prescribed in a patient's device or treatment prescription. Control unit 30 in an embodiment also calculates the patient's ultrafiltration ("UF") volume by subtracting the total fill volume from the total drain volume.

In one example, suppose after the vent step that 195 ml of hydraulic fluid is removed from inflatable bladder 80 within chamber 50 over a draw stroke. The first set of pressure measurements and the first ideal gas law determination then determines that there are three ml of air either in disposable container 102 or in between container 102 and chamber 50. The amount of fresh or used dialysis fluid in disposable container 102 after the draw stroke is therefore 195-3=192 ml. Next, 190 ml of hydraulic fluid is pumped into inflatable bladder 80 within chamber 50 over a discharge stroke. The second set of pressure measurements and the second ideal gas law determination then determines that there are two ml of air either in disposable container 102 or in between container 102 and chamber 50. Thus one ml of air has been pumped out of chamber 50 via the discharge stroke. Thus, of the 190 ml of some combination of fresh or used dialysis fluid and air displaced by hydraulic fluid, one ml is determined to be air. The amount of fresh or used dialysis fluid displaced is accordingly 190 ml less one ml of air or 189 ml.

The above example shows that it also known how much fresh or used dialysis fluid remains in container or bag 102 after the discharge or expel stroke, namely, the calculated amount of fresh or used dialysis fluid pulled into container or bag 102 less the calculated amount of fresh or used dialysis fluid discharged or expelled from container or bag 102. In the above example 192 ml of fluid is calculated to have been drawn in, while 189 ml of fluid is calculated to have been expelled. So the amount of fresh or used dialysis fluid remaining in container or bag 102 after the discharge stroke is three ml. It is accordingly contemplated to either repeat the first, venting step of FIG. 6 in the next draw and discharge sequence to start completely over or to begin instead with the second, draw step of FIG. 7 and then at the end add the remaining three ml of fresh or used dialysis fluid to the determined draw amount of fluid in FIG. 7.

It should be understood that various changes and modifications to the presently preferred embodiments described herein will be apparent to those skilled in the art. It is therefore intended that such changes and modifications be covered by the appended claims. For example, the end of a patient drain may be determined by control unit 30 detecting low effluent flowrate via the ideal gas law calculation discussed herein as opposed to draining to a prescribed drain. In another example, it is contemplated for control unit 30 to roughly control draw and discharge volumes by emptying and filling inflatable bladder 80, respectively, with varying but known amounts of incompressible fluid and then using the ideal gas law to determine a precise draw or discharge volume by removing the determined air volume. In this manner, a larger volume flexible container or bag 102 may be provided so as to be able to provide large volume draws and discharges efficiently, e.g., at the beginning of a patient fill or drain phase, but then to meter draw and discharge volumes more precisely at the end of the patient fill or drain phase.

The invention is claimed as follows:

1. A peritoneal dialysis system comprising:
- a chamber;
- a hydraulic pump;
- an inflatable bladder located within the chamber and in hydraulic fluid communication with the hydraulic pump;
- a pressure sensor positioned and arranged to sense pneumatic pressure within the chamber;
- a flexible container or bag removably placed inside the chamber, the flexible container or bag fluidly coupled to at least one fluid line and configured to receive fresh or used dialysis fluid;
- at least one valve fluidly located between the flexible container or bag and the at least one fluid line; and
- a control unit configured to:
  - determine (i) a first amount of air within the flexible container or bag and/or the chamber before a discharge stroke of the hydraulic pump via a first ideal gas law calculation when the at least one valve is closed by:
    - (a) taking a first pressure reading via the pressure sensor,
    - (b) causing a first measurement amount of hydraulic fluid to be metered into the inflatable bladder, and
    - (c) taking a second pressure reading via the pressure sensor for use with the first ideal gas law calculation,
  - determine (ii) a second amount of air within the flexible container or bag and/or the chamber after the discharge stroke of the hydraulic pump via a second ideal gas law calculation when the at least one valve is closed by:
    - (a) taking a first pressure reading via the pressure sensor,
    - (b) causing a second measurement amount of the hydraulic fluid to be metered into the inflatable bladder, and
    - (c) taking a second pressure reading via the pressure sensor for use with the second ideal gas law calculation, and
  - determine (iii) a discharge volume of the fresh or used dialysis fluid from the flexible container or bag for the discharge stroke of the hydraulic pump by subtracting a difference between the first amount of air and the second amount of air from a known amount of the hydraulic fluid metered to the inflatable bladder for the discharge stroke.

2. The peritoneal dialysis system of claim 1, wherein the pressure sensor is positioned and arranged to sense the pneumatic pressure within the chamber via sensing pressure of the hydraulic fluid acting as a pressure transmission medium.

3. The peritoneal dialysis system of claim 1, wherein the first measurement amount of the hydraulic fluid and the second measurement amount of the hydraulic fluid are at least substantially the same.

4. The peritoneal dialysis system of claim 1, wherein the control unit is further configured to determine a draw volume by subtracting the first amount of air before the discharge stroke from a second known amount of the hydraulic fluid metered from the inflatable bladder for a draw stroke.

5. The peritoneal dialysis system of claim 3, wherein the control unit is further configured to determine a volume of the fresh or used dialysis fluid remaining in the chamber after the discharge stroke by subtracting the discharge volume from the draw volume.

6. The peritoneal dialysis system of claim 5, wherein the control unit is further configured to use the volume of the fresh or used dialysis fluid remaining in the chamber for a repeat of the (i) to the (ii) to the (iii).

7. The peritoneal dialysis system of claim 1, further comprising a disposable set having the flexible container or bag insertable within the chamber, the flexible container or bag holding the discharge volume of the fresh or used dialysis fluid.

8. The peritoneal dialysis system of claim 7, wherein the disposable set includes at least one fluid source line and at least one fluid destination line in fluid communication with the flexible container or bag, and the at least one valve includes a fluid source valve for each fluid source line of the at least one fluid source line and a fluid destination valve for each fluid destination line of the at least one fluid destination line.

9. The peritoneal dialysis system of claim 8, wherein each fluid source valve and each fluid destination valve is closed during the (i) and the (ii).

10. The peritoneal dialysis system of claim 8, wherein the control unit is further configured to cause, prior to the (i), one of the fluid source valve to be open and for the hydraulic pump to pull the hydraulic fluid from the inflatable bladder to in turn pull the fresh or used dialysis fluid into the flexible container or bag in preparation for the discharge stroke.

11. The peritoneal dialysis system of claim 8, wherein the control unit is further configured to cause, prior to the (ii), one of the fluid destination valve to be open and for the hydraulic pump to push the hydraulic fluid into the inflatable bladder to in turn push the fresh or used dialysis fluid from the flexible container or bag for the discharge stroke.

12. The peritoneal dialysis system of claim 1, wherein the hydraulic pump includes a syringe barrel and a syringe plunger.

13. The peritoneal dialysis system of claim 1, wherein the hydraulic pump includes a hydraulic fluid storage area, and wherein the hydraulic fluid is able to be metered back and forth between the hydraulic fluid storage area and the inflatable bladder.

14. The peritoneal dialysis system of claim 1, further comprising a linear actuator positioned and arranged to cause the hydraulic pump to meter the known amount of the hydraulic fluid to the inflatable bladder.

15. The peritoneal dialysis system of claim 14, wherein the linear actuator includes a motor and a rotational to translational conversion device driven by the motor and in mechanical communication with the hydraulic pump.

16. The peritoneal dialysis system of claim 14, wherein the linear actuator includes a positional feedback device in operable communication with the control unit to provide positional feedback for the control unit to cause the known amount of the hydraulic fluid to be metered to the inflatable bladder.

17. The peritoneal dialysis system of claim 1, further comprising a vent valve in pneumatic communication with the chamber, wherein the control unit is further configured to cause the vent valve to open and the inflatable bladder to be filled with the hydraulic fluid to vent the air from the chamber prior to the (i) to the (ii) to the (iii).

18. The peritoneal dialysis system of claim 17, wherein the vent valve is closed during the (i) to the (ii) to the (iii).

19. The peritoneal dialysis system of claim 1, wherein the control unit is configured to repeat the (i) to the (ii) to the (iii) until accumulated discharge volumes determined in the (iii) meet a desired patient fill volume or a desired patient drain volume or until a drain condition is met.

20. A peritoneal dialysis system comprising:

a hydraulic pump;

a chamber;

an inflatable bladder located within the chamber and in hydraulic fluid communication with the hydraulic pump;

a pressure sensor positioned and arranged to sense pneumatic pressure within the chamber;

a flexible container or bag removably placed inside the chamber, the flexible container or bag fluidly coupled to at least one fluid line and configured to receive fresh or used dialysis fluid; and a control unit configured to cause (i) a draw stroke in which a measured amount of hydraulic fluid is removed from the inflatable bladder by the hydraulic pump to draw the fresh or used dialysis fluid into the flexible container or bag, (ii) a first air amount determination to be made by taking pressure measurements using the pressure sensor before and after attempting to compress air within the chamber, (iii) a discharge stroke in which a second measured amount of the hydraulic fluid is delivered to the inflatable bladder by the hydraulic pump to discharge the fresh or used dialysis fluid from the flexible container or bag, (iv) a second air amount determination to be made by taking pressure measurements using the pressure sensor before and after attempting to compress the air within the chamber, and (v) a discharge volume of the fresh or used dialysis fluid for the discharge stroke to be determined by subtracting a difference between the first air amount and the second air amount from the second measured amount of the hydraulic fluid delivered to the inflatable bladder for the discharge stroke.

21. The peritoneal dialysis system of claim 20, wherein the flexible container or bag holds the fresh or used dialysis fluid, and wherein in the (ii) and the (iv) attempting to compress the air includes attempting to compress the air within the flexible container or bag and between the flexible container or bag and the chamber.

22. The peritoneal dialysis system of claim 20, wherein attempting to compress the air within the chamber includes delivering the hydraulic fluid to the inflatable bladder.

23. The peritoneal dialysis system of claim 20, wherein the control unit is further configured to cause a draw volume of the fresh or used dialysis fluid in the flexible container or bag to be determined by subtracting the first air amount from the measured amount of the hydraulic fluid removed from the inflatable bladder.

24. The peritoneal dialysis system of claim 20, wherein the control unit is configured to repeat the (i) to the (ii) to the (iii) to the (iv) to the (v) until a desired patient fill volume, a desired patient drain volume, or a drain condition is met.

25. The peritoneal dialysis system of claim 20, wherein the first air amount determination and the second air amount determination are performed by the control unit using an ideal gas law evaluation of the pressure measurements taken before and after attempting to compress the air within the chamber.

* * * * *